US006774123B1

(12) United States Patent
Budowsky et al.

(10) Patent No.: US 6,774,123 B1
(45) Date of Patent: Aug. 10, 2004

(54) METHODS AND COMPOSITIONS FOR INACTIVATING VIRUSES

(75) Inventors: Edward I. Budowsky, Brookline, MA (US); Samuel K. Ackerman, Weston, MA (US); Andrei A. Purmal, Waltham, MA (US); Clark M. Edson, Somerville, MA (US); Martin D. Williams, Watertown, MA (US)

(73) Assignee: V.I. Technologies, Inc., Watertown, MA (US)

( * ) Notice: Subject to any disclaimer, the term of this patent is extended or adjusted under 35 U.S.C. 154(b) by 0 days.

(21) Appl. No.: 09/362,337

(22) Filed: Jul. 28, 1999

Related U.S. Application Data

(62) Division of application No. 09/005,719, filed on Jan. 12, 1998.

(51) Int. Cl.$^7$ .................. A61K 31/83; A61K 31/66; A61K 31/335; A61K 31/075; A61K 31/08

(52) U.S. Cl. .................. 514/183; 514/144; 514/148; 514/475; 514/720; 514/723

(58) Field of Search ................ 514/183, 144, 514/148, 475, 720, 723

(56) References Cited

U.S. PATENT DOCUMENTS

| | | | |
|---|---|---|---|
| 3,487,157 A | | 12/1969 | Pierce et al. |
| 3,636,196 A | * | 1/1972 | Bauer et al. .................. 424/89 |
| 4,429,045 A | | 1/1984 | Bass et al. |
| 4,567,042 A | | 1/1986 | Acree et al. |
| 4,820,805 A | * | 4/1989 | Neurath et al. ............. 530/410 |
| 4,841,023 A | * | 6/1989 | Horowitz ..................... 530/351 |
| 5,547,576 A | | 8/1996 | Onishi et al. |
| 5,691,132 A | | 11/1997 | Wollowitz et al. |
| 5,891,705 A | | 4/1999 | Budowsky et al. |
| 6,093,564 A | | 7/2000 | Budowsky et al. |
| 6,093,725 A | | 7/2000 | Cook et al. |
| 6,114,108 A | | 9/2000 | Budowsky |
| 6,136,586 A | | 10/2000 | Budowsky |
| 6,143,490 A | | 11/2000 | Cook et al. |
| 6,171,777 B1 | | 1/2001 | Cook et al. |
| 6,177,441 B1 | | 1/2001 | Cook et al. |
| 6,270,952 B1 | | 8/2001 | Cook et al. |
| 6,352,695 B1 | | 3/2002 | Budowsky et al. |
| 6,369,048 B1 | | 4/2002 | Budowsky et al. |
| 6,410,219 B1 | | 6/2002 | Cook et al. |

FOREIGN PATENT DOCUMENTS

| | | |
|---|---|---|
| EP | 0476 711 A2 | 3/1992 |
| EP | 0612532 A2 | 8/1994 |
| JP | 6-805520 A | 3/1994 |
| RO | RO 101400 | 4/1992 |
| SU | 1768636 A1 | 10/1992 |
| SU | 1809836 A3 | 4/1993 |
| SU | 594771 A1 | 7/1993 |
| WO | WO 92/03157 | 3/1992 |
| WO | WO 92/18161 | 10/1992 |
| WO | WO 96/14737 A1 | 5/1996 |
| WO | WO 96/39818 A1 | 12/1996 |
| WO | WO 96/39818 | 12/1996 |
| WO | WO 96/39820 A1 | 12/1996 |
| WO | WO 97/07674 A1 | 3/1997 |
| WO | WO 97/21346 A1 | 6/1997 |
| WO | WO 98/45415 A1 | 10/1998 |
| WO | WO 99/17802 A1 | 4/1999 |

OTHER PUBLICATIONS

US 6,331,387, 12/2001, Hei (withdrawn)

Armor, S,, and H.E. Webb, Use of N–Acetylethyleneimine [AEI] for the inactivation of Semliki Forest Virus in vitro J Medical Virology 19:367–376 (1986).

Atwell, G.J. et al., Synthesis, DNA Interactions and Biological Activity of DNA Minor Groove Targeted Polyberizamide–linked Nitrogen Mustards, Bioorg Med. Client. Jun. 1995; 3(6):679–91.

Briel, S. et al Identification of New Aqueous Chemical Degradation Products of Isophosphoramide Mustard J Pharm Biomed Anal. Jun. 2001;25 (3–4): 669–78.

Brown, F. et al. A Universal Virus Inactivant for Decontaminating Blood and Pharmaceutical Products Biologicals (1998) 26, 39–47.

Budowsky, E.I., Problems and prospects for preparation of killed antiviral vaccines Adv. Virus Res. 39:255–90 (1991).

Charache, S. et al.. Evaluation of Extracorporeal Alkylation of Red Cells as a Potential Treatment for Sickle Cell Anemia, Blood 1976; 47(3):481–88.

Danao T. et al., Nitrogen Mustard as Induction Therapy for Rheumatoid Arthritis: Clinical and Immunologic Effects. J. Rheum. 1991 19:1683–86.

Drake, M.E. et al., Effect of Nitrogen Mustard on Virus Serum Hepatitis in Whole Blood. Proc. of Soc. Exp. Rio. Med. 1952(80)310–13.

Ferguson, L.R. et al.. DNA–directed Aniline Mustards with High Selectivity for Adenine or Guanine Bases: Mutagenesis in a variety of *Salmonella typhimurium* Strains Differing in DNA–Repair Capability,' Mutat Res. Apr. 1994; 321(1–2):27–34.

Ferguson, L.R. et cal.. Bacterial Mutagenicity Studies of DNA–Intercalating Aniline Mustards: an Insight Into the Mode of Action of a Novel Class of Anti–Tumor Drugs, Anticancer Drug Des. Oct. 1989; 4(3):209–19.

Fries, K.M. et al 31P NMR and Chloride Ion Kinetics of Alkylating Monoester Phorphoramidates J. Med. Chem Feb. 1991;34(2):565–9.

(List continued on next page.)

Primary Examiner—Russell Travers
(74) Attorney, Agent, or Firm—Wolf, Greenfield & Sacks, P.C.

(57) ABSTRACT

Methods and compositions for selectively inactivating viruses in biological compositions, including contacting the composition with an organic solvent and an ethyleneimine oligomer inactivating agent, are disclosed.

33 Claims, 3 Drawing Sheets

OTHER PUBLICATIONS

Gao. Yi–Gui; Sriram, M. et cal.. Minor Groove Binding of SN6999 to an Alkylated DNA: Molecular Structure of d(CGC[e6G]AATTCGCG)–SN6999 Complex, Biochemistry Sep. 21, 1993; 32(37):9639–48.

Gourdie T.A. et al.. DNA–directed Alkylating Agents. I. Structure–activity Relationships for Acridine–linked Aniline Mustards: Consequences of Varying the Reactivity of the Mustard, J. Med. Chem. Apr. 1990; 33(4):1177–86.

Gourdie T.A. et al.. Synthesis and Evaluation of DNA–targeted Spatially Separated Bis(Aniline Mustards) as Potential Alkylating Agents with Enhances DNA Cross–linking Capability, J. Med. Chem. Jan. 1991; 34(1):240–8.

Gravatt, G.L. et al.. DNA–directed Alkylating Agents. 6. Synthesis and Antitumor Activity of DNA Tumor Groove–targeted Aniline Mustard Analogues of Pibenzimol, J. Med. Chem.. Dec. 9, 1994; 37(25):4338–45.

Gravatt, G.L. et al.. DNA–Directed Alkylating Agents 4. 4–Anilinoduinoline–Based Minor Groove Directed Aniline Mustards, J. Med Chem 1991, 34(5):1552–60.

Griffin, M.T. et al Kinetics of Activation and in Vivo Muscarinic Receptor Binding of N–(2–bromoethyl)–4–Piperidinyl Diphenylacetate: an Analog of 4–DAMP Mustard J. Pharmacol Exp Ther Jul. 1993; 266(1) 301–5.

Hamza, A. Quantum Molecular Modeling of the Interaction Between Guanine and Alkylating Agents—2—Nitrogen Mustard J. Biomol Struct Dyn Jun. 1996; 13(6):915–24.

Hartman, F.W. et al., Preparation and Sterilization of Blood Plasma. Ant. J. Clin. Path, 1954(24); 339–48.

Hartman, F.W. et al.. On the Chemical Sterilization of Blood and Blood Plasma. Proc. of Soc. Exp. Bio. Med. 1949;70:248–54.

Hartman, F.W., et al.. Four–Year Study Concerning the Inactivation of Viruses in Blood and Plasma, Presented at the 55th Annual Meeting of the American Gastroenterological Association, San Francisco, California, Jun. 1954.

Hassanain, M.M., Preliminary findings for an inactivated African horsesickness vaccine using binary ethyleneimine Revue Elev. Med. Vet Pays Trop. 45: 231–234 (1992).

Hemminiki, K. DNA Adducts of Nitrogen Mustards and Ethyleneimines DNA Adducts: Identification and Biological Significance, IARC Scientific Publications No. 125, Editors: Hemminki, et al., 1994, pp. 313–321.

Knorre, D.G. et al., Reactive Derivatives Of Oligonucleotides As Potential Antiviral Drugs, Problems of Virology, 1985, No. 5, pp. 524–'?.

Kohn, K.W. et al Mechanisms of DNA Sequence Selective Alkylation of Guanine–N7 Positions by Nitrogen Mustards Biochem Pharmacol May 1, 1988; 37(9): 1799–800.

Lee, M et al., In Vitro Cytotoxicity of GC Sequence Directed Alkylating Agents Related to Distamycin, J. Med. Cheer. Apr. 2, 1993; 36(7)863–70.

Lobastov, A.E., Use of ethyleneimine dimmer for the inactivation of infectious rhinotracheitis virus of cattle Probl. Virusol., Mol. Biol. Gistol. S–kh, Zhivotn., pp. 4–6 (1983) (& English translation).

LoGrippo, G.A et al.. Chemical and Combined Methods for Plasma Sterilization, 6th Congress of the Int'l Soc. ofBlood Trans., 1958, pp. 225–230.

Mattes, W.B. et al.. GC–rich Regions in Genomes as Targets for DNA Alkylation, Carcinogenesis 1988; 9(11):2065–72.

Prakash, A.S. et al., Differences in Sequence Selectivity of DNA Alkylation by Isomeric Intercalating Aniline Mustards, Chem. Biol. Interact. 1990; 76(23):241–8.

Price, C.O. et al Relative Reactivities for Monofunctional Nitrogen Mustard Alkylation of Nulceic Acid Components Biochim Biophys Acta Sep. 24, 1968; 166(2):327–59.

Roth, E.F. Jr. et al., Metabolic Effects of Antisickling Amounts of Nitrogen and Nor–Nitrogen Mustard on Rabbit and Human Erythrocytes. Blood 1975;45(6):779–88.

Springer, J.B. et al Isophosphoramide Mustard and Its Mechanism of Bisalkylation J. Org. Chem Oct. 16, 1998; 63(21):7218–7222.

Valu, K.K. et al., DNA–directed Alkylating Agents. 3. Structure–activity relationships for Acridine–linked Aniline Mustards: Consequences of Varying the Length of the Linker Chain. J. Med. Chem Nov. 1990; 33(11):3014–9.

Verschaeve, L. et a. "Mutagenicity of Ethyleneimine" Mutation Res. 238:39–55 (1990).

Vlasov, V.V. et al., –The Feasibility, Of Blocking Influenza Infections By Means Of Alkylating Derivatives Of Oligonucleotides, Molecular Genetics, Microbiology, And Virology, 1984, No. 11.

Warrington, Derivatives of Aziridine as Inactivants for Foot–and–Mouth Disease Virus Vaccines Am J. Vet. Res., vol. 34, No. 8. pp. 1087–1091.

Wickham, G. et al., DNA–binding Properties and Antitumour Activity of Monofunctional Alkylating Groups Attached to the DNA–intercalating Chromophore Phenanthridine: n–Brotnoalkylplienanthridinium Bromides, Biochimic ct Biopysica Aeta 1991 1073:528–37.

Wilke, W.S. et cal., Parenternal Nitrogen Mustard for Inflammatory Arthritis, C'lev. Clin. J. Med. Oct. 1990; 57(7):643–46.

Yamamoto, et al. Cancer Research 26, pt. 1, 2301–2306 (Nov. 1966).

Yang, C. et al The Preparation of an Inactivated Antigen for Bluetongue Serology Zentralbl Veterinarmed [B] May 1984; 31(4); 290–6.

Zalesskaya, M.A., Inactivation of viral genome by beta–p-ropiolactone and ethyleneimines using the bacteriophage MS–2 as an example, Russian State Library, Moscow, Russia (1988).

International search report for PCT/US96/14040 mailed Jan. 14, 1997.

International preliminary examination report for PCT/US96/14040 mailed Dec. 9, 1997, 6 pages.

Bahnemann, H.G., "Inactivation of Viral Antigens for Vaccine Preparation with Particular Reference to the Application of Binary Ethylenimine," *Vaccine,* 8:299–303 (1990).

Bahnemann, H.G., "Inactivation of Viruses in Serum with Binary Ethyleneimine," *Journal of Clinical Microbiology,* vol. 3, No. 2, pp. 209–210 (1975).

Budowsky, U.S. patent application Ser. No. 08/521,245, filed Aug. 29, 1995 entitled: "Methods and Compositions for the Selective Modification of Nucleic Acids."

Budowsky, U.S. patent application Ser. No. 08/705,045, filed Aug. 29, 1995 entitled: "Methods and Compositions for the Selective Modification of Nucleic Acids."

Budowsky, U.S. patent application Ser. No. 08/855,378 filed May 13, 1997, entitled: "Methods and Compositions for the Selective Modification of Nucleic Acids."

Budowsky et al., U. S. patent application Ser. No. 08/835,446 filed Apr. 8, 1997, entitled: "Methods for Inactivating a Virus."

Budowsky, U.S. patent application Ser. No. 08/835,446, filed Jan. 12, 1998, entitled: "Methods and Compositions for the Selective Modification of Nucleic Acids."

Budowsky et al., Inactivation of phage MS2 infectivity by the action of ethyleneimines, *Bioorg. Khim.* 11:989–991 (1985) (in Russian). English Abstract provided, 1 page.

Budowsky, and Zalesskaya, "Principles of selective inactivation of viral genome v. Rational selection of conditions for inactivation of the viral suspension infectivity to a given extent by the action of B–propiolactone," *Vaccine* 9:319–325 (1991).

Budowsky, et al., "Principles of Selective Inactivation of the Viral Genome, Dependence of the Rate of viral RNA Modification on the Number of Protonizable Groups in Ethyleneimine Oligomer," *Vaccine Res.,* 5(1):29–39 (1996).

Dermer, and Ham, Ethyleneimine and Other Aziridines, *Acad. Press,* NY—London, pp. 249–285 (1969).

Earley, et al., "Reactions of Ethyleneimine. IX. The Mechanisms of Ring Openings of Ethylenimine in Acidic Solutions," *J. Am. Chem. Soc.* 80:3458–3462 (1958).

Hemminki et al., "Reactions of ethyleneimine with guanosine and deocyguanosine," *Chem. Biol. Interactions,* 8:249–260 (1984).

Horowitz et al., "Viral safety of solvent/detergent–treated blood products," *Blood Coagulation and Fibrinolysis* 5:521–528 (1994).

Horowitz et al., "Elimination of disease–transmitting enveloped viruses from human blood plasma and mammalian cell products," *Bioseparation* 1:409–417 (1991).

King,"Evaluation of Different Methods of Inactivation of Newcastle Disease Virus and Avian Influenza Virus in Egg Fluids and Serum," *Avian Diseases* 35:505–514 (1991).

Kochetkov and Budowsky, eds., Organic Chemistry of Nucleic Acids, Part A, Plenum Press, London—New York, pp. 48–55 (1972).

Kostyanovskii et al., "Oligomers of azridines and N–beta–azridinoethylamides," Bulletin of the Academy of Sciences of the USSR, Division of Chemical Science vol. 37(11):2315–2325, May 29, 1989. (Translated from IzvestiyaAkademi Nauk SSR, Seriya Khimicheskaya 11:2566–2575).

O'Rourke et al., "Reactions of ethyleneimine with guanosine and deocyguanosine," *J. Am. Chem. Soc.* 78:2159–2160 (1956).

Prodouz et al., "Inhibition of Merocyanine 540–mediated Photosensitization of Platelets and Viruses," *Transfusion* 31:415–422 (1991).

Race et al., "An Experimental Chemically Inactivated HIV–1 Vaccine induces Antibodies that Neutralize Homologous and Heterologous Viruses," *Vaccine* 13(1):54–60 (1995).

Stevens, "Studies on the Interaction of Homologues of Spermine with Deoxyribonucleoic Acid and with Bacterial Protoplasts," *Biochem. J.* 103:811–815 (1967).

Tanirbergenov et al., "Regularities of mutagenic and toxic effects of ethyleneimine and its oligomers. A comparative study in the automated system SOS–chromotest and in standard bacterial test systems," *Genetika* 24:763 (1988) (in Russian) English translation provided, 5 pages.

Thomas et al., Ionic and Structural Effects on the Thermal Helix–Coil Transition of DNA Complexed with Natural and Synthetic Polyamines, *Biopolymers* 23:1295–1306 (1984).

Van Etten and Dolhum, "Effects of Hydrogen–Bond Formation by Phenols on the Conformational Equilibrium of trans–1,2–Dimethyl–3–isopropylaziridine," *J. Org. Chem.* 33:3904–3907 (1968).

Wagner et al., "Approaches to the Reduction of Viral Infectivity in Cellular Blood Components and Single Donor Plasma," *Transfusion Med. Rev.* V:18–32 (1991).

Budowsky et al, Vaccine Res. vol. 5(1) pp. 29–39, 1986.*

Hemminki, K., "Reactions of nitrogen mustards with DNA." IARC Sci. Publ. (1986) 78:55–70.

* cited by examiner

METHODS AND COMPOSITIONS FOR INACTIVATING VIRUSES

CROSS-REFERENCE TO RELATED APPLICATIONS

This application is a divisional application of and claims priority from U.S. patent application Ser. No. 09/005,719, filed Jan. 12, 1998.

BACKGROUND OF THE INVENTION

This invention relates to methods and compositions for inactivating viruses in biological compositions.

Transmission of viral diseases (e.g., hepatitis A, B, and C, acquired immunodeficiency syndrome, cytomegalovirus infections) by blood or blood products is a significant problem in medicine. The screening of donor blood for viral markers can help reduce the transmission of viruses to recipients, but many screening methods are directed to only a few discrete viruses and are therefore incomplete or less than 100% sensitive. Furthermore, other biological compositions, such as mammalian and hybridoma cell lines, products of cell lines, milk, colostrum, and sperm, can contain infectious viruses as well.

It is therefore important to inactivate viruses contained in donor blood, blood products, or other biological compositions. At the same time, it is desirable to leave the structure and function of valuable constituents, such as red blood cells, platelets, leukocytes, proteins, and polysaccharides, relatively unchanged.

A number of virus inactivating agents have been developed empirically. For example, formalin, beta-propiolactone, and gamma radiation have been used to inactivate viruses. In addition, ethyleneimine monomer has been used to inactivate foot-and-mouth disease virus and binary ethyleneimine (i.e., ethyleneimine monomer generated by a combination of two reagents) has been used to inactivate feline enteric coronavirus.

Many of these agents modify viruses nonspecifically; methods using these agents can therefore be difficult to standardize and apply reproducibly. Furthermore, many of these agents inactivate only some of the viruses present in a given biological composition.

SUMMARY OF THE INVENTION

The invention features a method of inactivating a virus in a biological composition; the method includes the steps of (a) contacting the composition with an organic solvent under viral inactivating conditions, where the organic solvent is selected from the group consisting of (i) trialkylphosphates of the formula $PO(OR^1)(OR^2)(OR^3)$, where each of $R^1$, $R^2$, and $R^3$ is, independently, $C_{1-10}$ alkyl, (ii) ethers of the formula $R^4$—O—$R^5$, where each of $R^4$ and $R^5$ is, independently, a $C_1$ to $C_{18}$ alkyl or alkenyl radical which can contain an oxygen or sulfur atom, and (iii) alcohols of the formula $R^6$—OH, where $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive, and (b) contacting the composition with an ethyleneimine oligomer inactivating agent under viral inactivating conditions, where steps (a) and (b) are performed less than 24 hours apart. Preferably, the inactivating agent is ethyleneimine dimer or ethyleneimine trimer.

A preferred method further includes the step of (c) contacting the composition with a nonionic detergent, such as polyoxyethylene sorbitan monooleate, under viral inactivating conditions, where steps (a), (b), and (c) are performed less than 24 hours apart. Preferred solvents include tri-n-butyl phosphate, ethers of the formula $R^4$—O—$R^5$, where each of $R^4$ and $R^5$ is, independently, a $C_1$ to $C_8$ alkyl radical, and alcohols of the formula $R^6$—OH, where $R^6$ is a $C_1$ to $C_8$ alkyl radical; a preferred detergent is polyoxyethylene sorbitan monooleate.

Preferably, steps (a), (b), and (c) are performed substantially simultaneously.

The invention also features a composition containing an organic solvent as described above, a non-ionic detergent, and an ethyleneimine oligomer inactivating agent.

The invention further features a method of inactivating a virus in a biological composition; the method includes the steps of (a) contacting the composition with an organic solvent under viral inactivating conditions, where the organic solvent is selected from the group consisting of (i) trialkylphosphates of the formula $PO(OR^1)(OR^2)(OR^3)$, where each of $R^1$, $R^2$, and $R^3$ is, independently, $C_{1-10}$ alkyl, (ii) ethers of the formula $R^4$—O—$R^5$, where each of $R^4$ and $R^5$ is, independently, a $C_1$ to $C_{18}$ alkyl or alkenyl radical which can contain an oxygen or sulfur atom, and (iii) alcohols of the formula $R^6$—OH, where $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive, and (b) contacting the composition with an inactivating agent under viral inactivating conditions, where the inactivating agent has the formula:

$$\underset{R_3}{\overset{R_1}{\diagdown}}\underset{R_4}{\overset{R_2}{\diagup}}N-[R_5-N^+(R_6,R_7)-]_n R_8 \cdot X^-_n$$

where each of $R_1$, $R_2$, $R_3$, $R_4$, $R_6$, $R_7$, and $R_8$ is, independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms, inclusive; X is a pharmaceutically acceptable counter-ion; and n is an integer between 1 and 10, inclusive, where steps (a) and (b) are performed less than 24 hours apart.

A preferred method further includes the step of (c) contacting the composition with a nonionic detergent under viral inactivating conditions, where steps (a), (b), and (c) are performed less than 24 hours apart. In another preferred method, steps (a), (b), and (c) are performed substantially simultaneously.

The invention also features a composition including an organic solvent as described above, a non-ionic detergent, and an inactivating agent, where the inactivating agent has the formula:

$$\underset{R_3}{\overset{R_1}{\diagdown}}\underset{R_4}{\overset{R_2}{\diagup}}N-[R_5-N^+(R_6,R_7)-]_n R_8 \cdot X^-_n$$

where each of $R_1$, $R_2$, $R_3$, $R_4$, $R_6$, $R_7$, and $R_8$ is, independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms, inclusive; X is a pharmaceutically acceptable counter-ion; and n is an integer between 1 and 10, inclusive.

The invention also features a method of inactivating a virus in a biological composition; the method includes the steps of (a) contacting the composition with an organic solvent under viral inactivating conditions, where the organic solvent is selected from the group consisting of (i) trialkylphosphates of the formula $PO(OR^1)(OR^2)(OR^3)$, where each of $R^1$, $R^2$, and $R^3$ is, independently, $C_{1-10}$ alkyl, (ii) ethers of the formula $R^4$—O—$R^5$, where each of $R^4$ and $R^5$ is, independently, a $C_1$ to $C_{18}$ alkyl or alkenyl radical which can contain an oxygen or sulfur atom, and (iii) alcohols of the formula $R^6$—OH, where $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive, and (b) contacting the composition with an inactivating agent under viral inactivating conditions, where the inactivating agent has the formula where $X_1$ is Cl or Br; $R_1$ is a divalent hydrocarbon moiety containing between 2 and 4 carbon atoms, inclusive; each of $R_2$, $R_3$, and $R_4$ is, independently, H or a monovalent hydrocarbon moiety containing between 1 and 4 carbon atoms, inclusive; $X_2$ is a pharmaceutically acceptable counter-ion; and n is an integer between 2 and 10, inclusive, where steps (a) and (b) are performed less than 24 hours apart. Preferably, $R_1$ is ethylene; $R_2$, $R_3$, and $R_4$ are H; and n is 3 or 4.

A preferred method further includes the step of (c) contacting the composition with a nonionic detergent under viral inactivating conditions, where steps (a), (b), and (c) are performed less than 24 hours apart. In another preferred method, steps (a), (b), and (c) are performed substantially simultaneously.

The invention further features a composition including an organic solvent as described above, a non-ionic detergent, and an inactivating agent, where the inactivating agent has the formula:

where $X_1$ is Cl or Br; $R_1$ is a divalent hydrocarbon moiety containing between 2 and 4 carbon atoms, inclusive; each of $R_2$, $R_3$, and $R_4$ is, independently, H or a monovalent hydrocarbon moiety containing between 1 and 4 carbon atoms, inclusive; $X_2$ is a pharmaceutically acceptable counter-ion; and n is an integer between 2 and 10, inclusive.

In addition, the invention features a method of inactivating a virus in a biological composition; the method includes the steps of (a) contacting the composition with an organic solvent under viral inactivating conditions, where the organic solvent is selected from the group consisting of (i) trialkylphosphates of the formula $PO(OR^1)(OR^2)(OR^3)$, where each of $R^1$, $R^2$, and $R^3$ is, independently, $C_{1-10}$ alkyl, (ii) ethers of the formula $R^4$—O—$R^5$, where each of $R^4$ and $R^5$ is, independently, a $C_1$ to $C_{18}$ alkyl or alkenyl radical which can contain an oxygen or sulfur atom, and (iii) alcohols of the formula $R^6$—OH, where $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive, and (b) contacting the composition with an inactivating agent under viral inactivating conditions, where the inactivating agent has the formula:

where $X_1$ is Cl or Br; each of $R_1$, $R_3$, $R_4$, and $R_5$ is, independently, H or a monovalent hydrocarbon moiety containing between 1 and 4 carbon atoms, inclusive; $R_2$ is a divalent hydrocarbon moiety containing 3 or 4 carbon atoms; $X_2$ is a pharmaceutically acceptable counter-ion; and n is an integer between 1 and 10, inclusive, where steps (a) and (b) are performed less than 24 hours apart.

A preferred method further includes the step of (c) contacting the composition with a nonionic detergent under viral inactivating conditions, where steps (a), (b), and (c) are performed less than 24 hours apart. In another preferred method, steps (a), (b), and (c) are performed substantially simultaneously.

Finally, the invention features a composition including an organic solvent as described above, a non-ionic detergent, and an inactivating agent, where the inactivating agent has the formula:

where $X_1$ is Cl or Br; each of $R_1$, $R_3$, $R_4$, and $R_5$ is, independently, H or a monovalent hydrocarbon moiety containing between 1 and 4 carbon atoms, inclusive; $R_2$ is a divalent hydrocarbon moiety containing 3 or 4 carbon atoms; $X_2$ is a pharmaceutically acceptable counter-ion; and n is an integer between 1 and 10, inclusive.

"INACTINE™ agents" refers to compounds of the invention having (1) an aziridino moiety or a halo-hydrocarbon-amino moiety, such as a β-ethyl-amino moiety, and (2) two or more nitrogen atoms separated by hydrocarbon moieties. These compounds are also referred to as "inactivating agents," or "selective inactivating agents."

An inactivating agent has "selectivity" for nucleic acids or "selectively" reacts with nucleic acids if the comparative rate of reaction of the inactivating agent with nucleic acids is greater than the rate of reaction with other biological molecules, e.g., proteins, carbohydrates or lipids.

"Nucleic acid" refers to both single and double stranded DNA and RNA.

"Biological composition" refers to a composition containing or derived from cells or biopolymers. Biological compositions include, for example, whole blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascitic fluid, proteins present in blood cells, and products produced in cell culture by normal or transformed cells (e.g., via recombinant DNA or monoclonal antibody technology). Biological compositions can be cell-free.

"Biopolymer" or "biological molecule" refers to any class of organic molecule normally found in living organisms including, for example, nucleic acids, polypeptides, post-translationally modified proteins (e.g., glycoproteins), polysaccharides, and lipids.

"Inactivating," "inactivation," or "inactivate," when referring to nucleic acids, means to substantially eliminate the template activity of DNA or RNA, for example, by destroying the ability to replicate, transcribe, or translate a message. When referring to viruses, the term "inactivating" means diminishing or eliminating the number of infectious viral particles measured as a decrease in the infectious titer or number of infectious virus particles per ml. Such a decrease in infectious virus particles is determined by assays well known to a person of ordinary skill in the art.

"Viral inactivating conditions" refer to the conditions under which the viral particles are incubated with the inactivating compositions of this invention, including, for example, time of treatment, pH, temperature, salt composition, and concentration of selective inactivating agent, so as to inactivate the viral genome to the desired extent. Viral inactivating conditions are selected from the conditions described below for the selective inactivation of viruses in biological compositions.

"Virus" refers to DNA and RNA viruses, viroids, and prions. Viruses include both enveloped and non-enveloped viruses, for example, hepatitis A virus, hepatitis B virus, poxviruses, herpes viruses, adenoviruses, papovaviruses, parvoviruses, reoviruses, orbiviruses, picornaviruses, rotaviruses, alphaviruses, rubivirues, influenza virus, type A and B, flaviviruses, coronaviruses, paramyxoviruses, morbilliviruses, pneumoviruses, rhabdoviruses, lyssaviruses, orthmyxoviruses, bunyaviruses, phleboviruses, nairoviruses, hepadnaviruses, arenaviruses, retroviruses, enteroviruses, rhinoviruses and the filoviruses.

"Ethyleneimine oligomers" refer to compounds of the formula:

$$\triangleright N-(CH_2-CH_2-NH-)_nH$$

where n is an integer from 1 to 10, inclusive, and salts thereof. The compounds can be linear or branched.

The methods and compositions of the present inventions provide advantages over other approaches to inactivating viruses in biological compositions. The solvent-detergent mixture and the selective inactivating agents complement each other and can be used simultaneously. The simultaneous treatment of biological compositions with two different inactivating agents provides a relatively fast, inexpensive method for inactivating a wide variety of viruses. Furthermore, since INACTINE™ agents are selective for nucleic acids and solvent-detergent mixtures are selective for the lipid coating of lipid-containing viruses, valuable components of the biological composition, such as proteins and carbohydrates, are left intact.

Other features and advantages of the invention will be apparent from the following description and from the claims.

DETAILED DESCRIPTION

The invention features methods for inactivating viruses in a biological composition by contacting the composition with a combination of inactivating agents. More particularly, the invention features methods for inactivating viruses in a biological composition by contacting the composition with (a) an INACTINE™ agent (i.e., a selective inactivating agent) and (b) an organic solvent, or an organic solvent-detergent combination.

Selective Inactivating Agents

The selective inactivating agents of the present invention include ethyleneimine oligomers, substituted aziridino compounds, and related halo-hydrocarbon-amino compounds.

For example, ethyleneimine oligomers having the formula:

$$\triangleright N-(CH_2-CH_2-NH-)_nH$$

where n is an integer from 1 to 10, inclusive, and salts thereof, can be used. For example, the dimer $$\triangleright N-CH_2-CH_2-NH_2$$

trimer $$\triangleright N-CH_2-CH_2-NH-CH_2-CH_2-NH_2$$

linear tetramer $$\triangleright N-CH_2-CH_2-NH-CH_2-CH_2-NH-CH_2-CH_2-NH_2$$

and branched tetramer $$\triangleright N-CH_2-CH_2-N\begin{matrix}CH_2-CH_2-NH_2\\ \\ CH_2-CH_2-NH_2\end{matrix}$$

of ethyleneimine can be used as the selective inactivating agent. These compounds can be prepared as described in Kostyanovskii et al. (translated from *Izvestiya Akademii Nauk SSSR*, Seriya Khimicheskaya, 11:2566–2577, 1988). Preferred compounds include ethyleneimine dimer and ethyleneimine trimer.

The selective inactivating agents of the invention can also have the formula:

$$\begin{matrix}R_1 & R_2\\ & \\ & \end{matrix}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!$$

$$\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!N-[R_5-N^+(R_6,R_7)-]_nR_8\cdot X^-_n$$

$$\begin{matrix}R_3 & R_4\end{matrix}$$

where each of $R_1$, $R_2$, $R_3$, $R_4$, $R_6$, $R_7$, and $R_8$ is, independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms, inclusive; X is a pharmaceutically acceptable counter-ion; and n is an integer between 1 and 10, inclusive. These compounds can be prepared as described in Budowsky et al., U.S. Ser. No. 08/943,643, filed Oct. 3, 1997.

Other compounds that can be used as selective inactivating agents include halo-hydrocarbon-amino compounds having the formula $\omega\text{-}X_1\text{—}[R_1\text{—}N^+(R_2, R_3)\text{—}]_n R_4\text{.}(X_2^-)_n$, where $X_1$ is Cl or Br; $R_1$ is a divalent hydrocarbon moiety containing between 2 and 4 carbon atoms, inclusive; each of $R_2$, $R_3$, and $R_4$ is, independently, H or a monovalent hydrocarbon moiety containing between 1 and 4 carbon atoms, inclusive; $X_2$ is a pharmaceutically acceptable counter-ion; and n is an integer between 2 and 10, inclusive. These compounds can be prepared as described in Budowsky et al., U.S. Ser. No. 08/855,378, filed May 13, 1997 and Budowsky et al., U.S. Ser. No. 08/943,643, filed Oct. 3, 1997.

Alternatively, these compounds can have the formula $\omega\text{-}X_1\text{—}CH_2CH_2\text{—}N^+H(R_1)\text{—}[R_2\text{—}N^+(R_3, R_4)\text{—}]_n R_5 \cdot (X_2^-)_{n+1}$, where $X_1$ is Cl or Br; each of $R_1$, $R_3$, $R_4$, and $R_5$ is, independently, H or a monovalent hydrocarbon moiety containing between 1 and 4 carbon atoms, inclusive; $R_2$ is a divalent hydrocarbon moiety having 3 or 4 carbon atoms; $X_2$ is a pharmaceutically acceptable counter-ion; and n is an integer between 1 and 10, inclusive. These compounds can be prepared as described in Budowsky et al., U.S. Ser. No. 08/943,643, filed Oct. 3, 1997.

The selective inactivating agents modify the nucleic acids of the viruses. The nucleic acids of the viruses in the composition are chemically modified at rates much faster than those of the other biological molecules. These agents are therefore useful when a practitioner wishes to modify the nucleic acids of viruses, while leaving other biological molecules relatively unchanged.

The selective inactivating agents described above have multiple positively charged atoms, i.e., they are oligocations. They therefore have a high affinity for oligoanions. As nucleic acids are the major polyanionic components of viruses, the selective inactivating agents bind selectively to viral nucleic acid, rather than to other virion components. The association constant is proportional to the oligocation and oligoanion volume charge densities and therefore increases with the total average positive charge of the oligocation. Longer oligomers will have a higher total average positive charge, leading to an increase in their association constant with oligoanions.

In addition, the distances between the positively charged nitrogen atoms of the inactivating agents are similar to the distances between the internucleotide phosphate groups (which are negatively charged) of polynucleotides; this further facilitates the binding of the selective inactivating agents to nucleic acids.

The inactivating agents modify nucleic acids through the reaction of the aziridino group, or through the reaction of the terminal halo-hydrocarbon-amino group with the nucleic acid bases in polynucleotides. The action of these compounds on polynucleotides leads to amino-alkylation of nucleophilic groups in the nucleic acid bases.

The reactivity of aziridines as electrophilic agents increases dramatically with the protonation of the aziridine nitrogen. Therefore, the form of these compounds protonated at the aziridino group is the more reactive form. The rates of usual electrophilic reactions of aziridines should be directly proportional to the concentration of their protonated forms in the complexes with polynucleotides.

The degree of protonation depends, in part, upon pH. In solution, the pK of the aziridino group decreases markedly as the total positive charge of the molecule increases. At a pH of about 7.0, the proportion of reactive aziridino groups in many inactivating agents is low. However, after association with a polyanion, the pK of the aziridino group increases significantly. Therefore, when the aziridino compound binds to a nucleic acid, the fraction of reactive aziridino groups increases locally.

Aziridines, like many electrophilic agents, modify nucleic acids preferentially at N7, N3, and N1 of purines and to a much lesser extent at N3 of pyrimidines. Template synthesis is arrested by alkylating agents primarily due to opening of the imidazole ring of N7 alkylated purines, predominantly of guanine. For example, aziridine modifies guanosine to produce N7(aminoethyl)-guanosine which displays a much higher rate of imidazole ring opening than does N7-alkylguanosine.

In the absence of repair or recombination, the modification of the nucleotide bases blocks replication, transcription, and translation of the viral genome and renders the virus non-infectious.

As the above discussion illustrates, it is the electrostatic interactions between the positively charged groups on the selective inactivating agent and the negatively charged phosphate groups on the DNA and RNA backbones that result in the selectivity of the selective inactivating agent for nucleic acids. The exact structures of the selective inactivating agents are therefore not as critical as, for example, the structures of many pharmaceutically useful compounds. For example, a change in one of the R substituents from a methyl group to an ethyl group will not significantly affect a selective inactivating agent's ability to selectively modify nucleic acids over other biomolecules.

It is important that the reactive part of the molecule (i.e., the aziridino group or the halo-hydrocarbon-amino group) remains reactive. For example, the aziridine ring will lose some of its reactivity if it is substituted by more than two hydrocarbon groups.

In addition, if the compounds contain hydrocarbon groups that have more than 4 carbon atoms, the compounds become lipophilic. Lipophilicity is undesired, as it will cause the agents to modify compounds such as proteins. Aromatic rings are also undesirable substituents, as aromatic rings can intercalate in the DNA or RNA. The resulting change in the DNA or RNA structure can disrupt the binding of the inactivating agents of the invention with the DNA or RNA.

The compounds of the invention contain at least 2 N atoms. Compounds with at least 3 N atoms are preferred, as these compounds have a higher total average positive charge, leading to an increase in their association constant with polynucleotides. In particular, compounds with 3 or 4 N atoms are preferred.

All these data and considerations allow one to select a selective inactivating agent, with the desired polynucleotide affinity. The selective inactivating agents can be used in concentrations of from 0.0001 M to 0.05 M, preferably from 0.0005 M to 0.005M.

Organic solvents

Organic solvents selectively inactivate viruses as well; they inactivate lipid containing viruses by disrupting the lipid envelopes of these viruses. The solvent does not disrupt the structure of other particles, such as proteins. Therefore, when a biological composition such as blood plasma is contacted with an organic solvent, the lipid containing viruses are virtually entirely inactivated; at the same time, the proteins are not substantially denatured.

Organic solvents that can be used in the present invention include trialkylphosphates of the formula $PO(OR^1)(OR^2)(OR^3)$, where each of $R^1$, $R^2$, and $R^3$ is, independently, $C_{1-10}$ alkyl. Specific examples include tri-(n-butyl)phosphate, tri-(t-butyl)phosphate, tri-(n-hexyl)phosphate, tri-(2-ethylhexyl)phosphate, and tri(n-decyl)phosphate. A preferred trialkylphosphate is tri-(n-butyl)phosphate (TNBP).

Trialkylphosphates having different alkyl chains, for example, ethyl, di(n-butyl) phosphate, can be used as well. Furthermore, mixtures of different trialkylphosphates can be used.

Ethers having the formula $R^4$—O—$R^5$, where each of $R^4$ and $R^5$ is, independently, a $C_1$–$C_{18}$ alkyl or alkenyl radical which can contain an oxygen or sulfur atom, can be used as the organic solvent as well. Preferably, each of $R^4$ and $R^5$ is, independently, $C_1$–$C_8$ alkyl. Preferred ethers include dimethyl ether, diethyl ether, ethyl propyl ether, methyl-butyl ether, methyl isopropyl ether and methyl isobutyl ether.

Alcohols having the formula $R^6$—OH, where $R^6$ is a $C_1$ to $C_{18}$ alkyl or alkenyl radical which can contain 1 to 4 oxygen or sulfur atoms, inclusive, in the chain and which can be substituted by 1 to 4 hydroxy groups, inclusive, can also be used as the organic solvent.

Preferred alcohols are those in which $R^6$ is a $C_1$ to $C_8$ alkyl, for example, methanol, ethanol, propanol, isopropanol, n-butanol, isobutanol, n-pentanol and isopentanol.

The organic solvent is used at a concentration of about 0.01% to about 1.0% (v/v), preferably about 0.1% to about 0.5% (v/v).

Nonionic Detergents

Preferably, a nonionic detergent is used in conjunction with the organic solvent. The detergent can be added before, at the same time, or after the organic solvent contacts the biological composition. The function of the detergent is to enhance the contact of the virus in the biological composition with the organic solvent.

The detergents of the invention are non-toxic, nonionic detergents that disperse at least 0.1% by weight of the fat in an aqueous solution when 1 gram detergent per 100 ml solution is introduced into the solution. Preferred detergents include polyoxyethylene derivatives of fatty acids, partial esters of sorbitol anhydrides (e.g., those available from Sigma Chemical Company under the trade names "Tween 80," "Tween 20," and "Polysorbate 80"), and nonionic oil soluble water detergents, such as oxyethylated alkylphenol (available from Sigma Chemical Company under the trade name "Triton X 100"). Other detergents that can be used include nonionic detergents such as octyl-beta-D-glucopyranoside.

The amount of detergent used is not crucial; concentrations of about 0.001% to about 10% (v/v), preferably about 0.1% to about 1.5% (v/v), can be used.

Preferably, the organic solvents and detergents are removed after the viruses in the biological compositions have been inactivated. For example, volatile solvents, such as low molecular weight ethers and alcohols, can be removed by subjecting the mixture to a temperature of 4° C. to 37° C. under a slight vacuum, for example using a rotary evaporator. Other methods include bubbling nitrogen gas through the mixture or lyophilizing the mixture. Non-volatile solvents, such as tri-n-butyl phosphate, and detergents can be separated from the desired components of the biological compositions by performing diafiltration using microporous membranes that retain the desired components of the mixtures; absorbing the desired components on chromatographic or affinity chromatographic supports; or precipitating the desired components.

As discussed above, selective inactivating agents and solvent-detergent mixtures inactivate viruses through different mechanisms. Solvent-detergent mixtures inactivate lipid containing viruses by disrupting the lipid envelope of the viruses. These mixtures inactivate only lipid enveloped viruses and leave the DNA or RNA of the virus unmodified, and therefore potentially infectious.

The selective inactivating agents of the invention inactivate viruses by modifying the nucleic acids of the viruses. Both solvent-detergent mixtures and these inactivating agents are selective for viruses; that is, they both inactivate viruses, while leaving other components of biological compositions, such as proteins, substantially unchanged.

The use of INACTINE™ agents and solvent-detergent mixtures in combination is therefore a powerful method for inactivating viruses. Since INACTINE™ agents and solvent-detergent mixtures inactivate viruses by different mechanisms, the combination can be used to inactivate a wide variety of viruses present in a biological composition. The biological composition can contain enveloped and/or non-enveloped viruses.

Viruses can be inactivated by contacting a composition containing the virus with a mixture having a concentration of about 0.0001 M to about 0.05 M selective inactivating agent, preferably about 0.0005 M to about 0.005 M; about 0.01% to about 1.0% (v/v) organic solvent, preferably about 0.1% to about 0.5%; about 0.001% to about 10% (v/v) detergent, preferably about 0.1% to about 1.5%; an ionic strength of about 0.01 M to about 0.5 M; and a pH of about 6.5 to about 7.5. The selection of pH depends, in part, on the stability of the virion. The practitioner can adjust the pH of the solution using many buffers customarily used in the art to handle biopolymers or cells, such as acetate, HEPES, MOPS, and so forth. The inactivation can take place at a temperature of about 4° C. to about 45° C., and for a time period of from 1 minute to 24 hours.

A biological composition can be first contacted with a selective inactivating agent, and then with a solvent-detergent mixture; alternatively, the order of the contacting steps can be reversed. In this case, each step can take place for a time period of 1 minute to 24 hours. The composition can also be contacted with a selective inactivating agent and a solvent-detergent mixture simultaneously. In this case, the inactivating step can take place for a time period of 1 minute to 24 hours. The latter method is advantageous, as it is more convenient, less time consuming, and less expensive. As the examples show, INACTINE™ agents and solvent-detergent mixtures are compatible and can be used simultaneously to inactivate different viruses.

A decrease in infectivity of "6 logs by measurement" in a cell- or biopolymer-containing composition means that a virus is inactivated to the extent determined by infectivity studies, where that virus is present in the untreated serum in such a concentration that even after dilution to $10^6$, viral activity can be measured. Different viruses can be produced to different titers. When a specific virus cannot be produced to a titer of $10^6$, inactivation is determined by direct quantitation measured up to the titer of virus produced. When the methods of the invention are used, the titer of the virus in a biological composition preferably decreases by at least about 4 logs by measurement.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims. Furthermore, the methods of the invention can be combined with still other modes of inactivating viruses.

Without further elaboration, it is believed that one skilled in the art can, based on the description herein, utilize the present invention to its fullest extent. The following specific examples are, therefore, to be construed merely as illustrative, and not limitative of the remainder of the disclosure in any way whatsoever. Publications mentioned herein are hereby incorporated by reference.

EXAMPLE 1
Kinetics of Bacteriophage Infectivity Inactivation

Ethyleneimine trimer is known to inactivate the infectivity of bacteriophage MS2. The ability of the trimer to inactivate the infectivity of MS2 in the presence of TNBP and Tween 80 was determined as follows.

A stock of bacteriophage MS2 (ATCC number 15597-B1) was prepared according to conventional procedures (D. L. Rogerson and G. Rushizky, *Analytical Biochemistry* 67: 675–678 (1975)). Purification was performed by sedimentation of bacteriophage in the presence of 6% polyethylene glycol (PEG 8000, USB) as described in K. Yamamoto and B. Alberts, *Virology* 40: 734–744 (1970).

Purified phage were suspended in 0.15 M NaCl solution (final bacteriophage stock titer was $5 \times 10^{13}$ pfu/ml) and stored at 4° C. The infectivity (titer) of phage suspension was determined by conventional bilayer technique on LB agar with the $F^+$ strain of *Escherichia coli* C-3000 (ATCC number 15597).

Ethyleneimine trimer was prepared as described above. A stock solution of the trimer was prepared immediately before use by the addition of trimer to 0.1 M MOPS, 50 mM NaCl to yield a solution with a trimer concentration of 1.23 mM and a pH of 7.13.

A 10×stock solution containing 3% (v/v) TNBP (FW 266.3, d=0.979, Sigma catalog number T-4908, lot number 96H3492) and 10% (v/v) Tween 80 (Polyoxyethylene sorbitan monooleate, FW 1309.68, d=1.064, Sigma catalog number P-8074, lot number 86H07841) was prepared by combining 30 µl TNBP and 100 µl Tween 80 with 870 µl 0.1 M MOPS, NaCl 50 mM, pH 7.13.

Three reaction mixtures were prepared.

(a) The first mixture contained 180 µl trimer stock solution, 22.2 µl 0.1 M MOPS, 50 mM NaCl, pH 7.13, and 20 µl bacteriophage MS2 stock.

(b) The second mixture contained 180 µl trimer stock solution, 22.2 µl TNBP-Tween 80 10×stock solution, and 20 µl bacteriophage MS2 stock. In both mixtures (a) and (b), the final concentration of trimer was 1 mM.

(c) The third (control) mixture contained 180 µl 0.1 M MOPS, 50 mM NaCl, pH 7.13, 22.2 µl TNBP-Tween 80 10×stock solution, and 20 µl bacteriophage MS2 stock.

Figure 1:
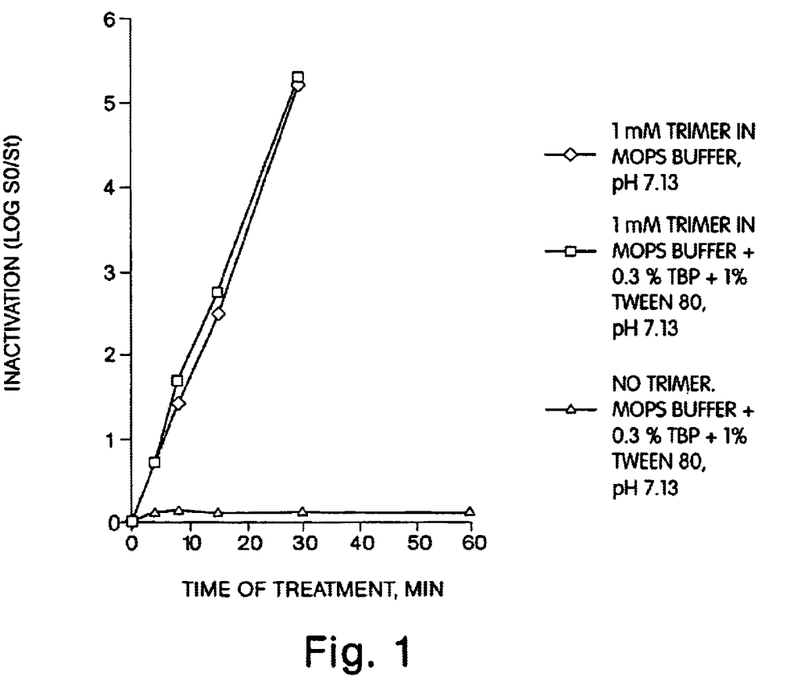
FIG. 1 is a graph showing log values of $MS_2$ infectivity inactivation versus time of treatment, using ethyleneimine trimer, a solvent-detergent mixture, and a combination of ethyleneimine trimer and a solvent-detergent mixture.

Aliquots of the reaction mixture incubated at 23° C. were taken at five defined time intervals. MS2 infectivity inactivation (log $S_0/S_t$, where $S_0$ and $S_t$ are the infectivity (titer) of the suspension before and t min after the start of inactivation) was determined at these five points. The results are shown in FIG. 1. As shown there, the control reaction mixture (designated by triangles) containing 0.3% TNBP and 1% Tween 80 showed an almost background level of MS2 infectivity inactivation. The reaction mixture containing 1 mM trimer (designated by diamonds) and the reaction mixture containing 1 mM trimer, 0.3% TNBP, and 1% Tween 80 (designated by squares) showed essentially the same infectivity inactivation after 30 minutes of incubation. These results illustrate that the presence of the solvent-detergent mixture does not impair the ability of ethyleneimine trimer to inactivate the infectivity of MS2.

EXAMPLE 2
Cytotoxicity Test

The effect of a solvent-detergent mixture on the viability of cells was determined as follows. A solution containing 0.1M MOPS buffer, 50 mM NaCl, 1% (v/v) Tween 80, 0.3% (v/v) TNBP, and having a pH of 7.13 was prepared. Serial two-fold dilutions of this solution were prepared to a final dilution of 1:2048, using 0.1M MOPS, 50 mM NaCl as the diluent. MDBK cells (Madin-Darby bovine kidney cells, passage 198) and PT-1 cells (porcine testis cells, passage 197) were cultured on 96-well tissue culture plates in MEM containing 5% goat serum or 10% fetal bovine serum, respectively. For the test, the growth medium was removed from the cells and replaced with 100 µl of each dilution; the plates were then incubated at 37° C. for 1 hour. After this time, the diluted solutions were removed and replaced with growth medium. The cells were examined at this time, and again after five days of incubation at 37° C. in a $CO_2$ incubator. After 1 hour at 37° C., the cells exposed to the dilutions of up to 1:32 (i.e., 1:2, 1:4, etc.) appeared to be lysed and were no longer viable. Cells exposed to dilutions of 1:64 and higher (i.e., 1:128, 1:256, etc.) appeared unaffected and were viable. After five days, the cells exposed to these dilutions were still viable, and cell growth was not inhibited. These results demonstrate that when dilutions of 1:64 or higher of the 1% Tween 80, 0.3% TNBP solution are used, it can be expected that a negligible percentage of any cell growth inhibition observed is due to the solvent-detergent mixture.

EXAMPLE 3
Inactivation of Bovine Viral Diarrhea Virus (BVD)

BVD is a lipid-enveloped virus, and can therefore be inactivated with solvent-detergent mixtures. The ability of a solvent-detergent mixture to inactivate BVD in the presence of ethyleneimine dimer was determined as follows.

A detergent stock solution (1% (v/v) Tween 80, 0.3% (v/v) TNBP in 0.1 M MOPS, 50 mM NaCl, pH 7.13) was prepared. A 5% dimer stock solution was prepared with 250 µl of 0.1 M MOPS, NaCl 50 mM, pH 7.0, and 12.5 µl dimer (ethyleneimine dimer, Dalton Chemical Laboratories, Inc., lot number LB-4-69A-03319). In addition, a quenching solution with a sodium thiosulphate concentration of 0.1M in 0.1 M MOPS, pH 7.0, was prepared.

(a) 8.9 ml 0.1 M MOPS, 50 mM NaCl, pH 7.0 was combined with 100 µl dimer stock solution. 1.0 ml BVD (stock #5) was added. The concentration of dimer in the resulting solution was 0.05%. The mixture was incubated at room temperature for a given time period (10 minutes, 30 minutes, or 1 hour). After this period, 1.85 ml of the solution was removed, and 0.15 ml quenching solution (0.1 M sodium thiosulphate in 0.1 M MOPS, pH 7.0) was added; quenching occurred over a period of 30 minutes at room temperature. The concentration of sodium thiosulphate in the final solution was 75 mM.

(b) 9 ml detergent stock solution was combined with 1.0 ml BVD. The mixture was incubated for a given time period (10 minutes, 30 minutes, or 1 hour) at room temperature. A 2 ml aliquot was removed at each time point for assay.

(b') 9 ml detergent stock solution was combined with 1.0 ml BVD. The mixture was incubated for a given time period (10 minutes, 30 minutes, or 1 hour) at room temperature. After the given time period, 1.85 ml of the mixture was removed, and 0.15 ml quenching solution was added; quenching occurred over a period of 30 minutes at room temperature. The concentration of sodium thiosulphate in the final solution was 75 mM.

(c) 8.9 ml detergent stock solution was combined with 100 µl dimer stock solution and 1.0 ml BVD. The concentration of dimer in the resulting solution was 0.05%. The mixture was incubated for a given time period (10 minutes, 30 minutes, 1 hour) at room temperature. After this period, 1.85 ml of the solution was removed and 0.15 ml quenching solution was added; quenching occurred over a period of 30 minutes at room temperature. The concentration of sodium thiosulphate in the final solution was 75 mM.

Serial 10-fold dilutions of the samples were prepared for assay. The growth medium was removed from MDBK cells grown on 96-well plates and replaced with 100 $\mu$l of the dilutions. After 1 hour at 37° C., these dilutions were discarded and replaced with 200 $\mu$l of MEM containing 5% goat serum. The wells were cultured at 37° C. for five days, then were formalin-fixed and stained with crystal violet.

Figure 2:
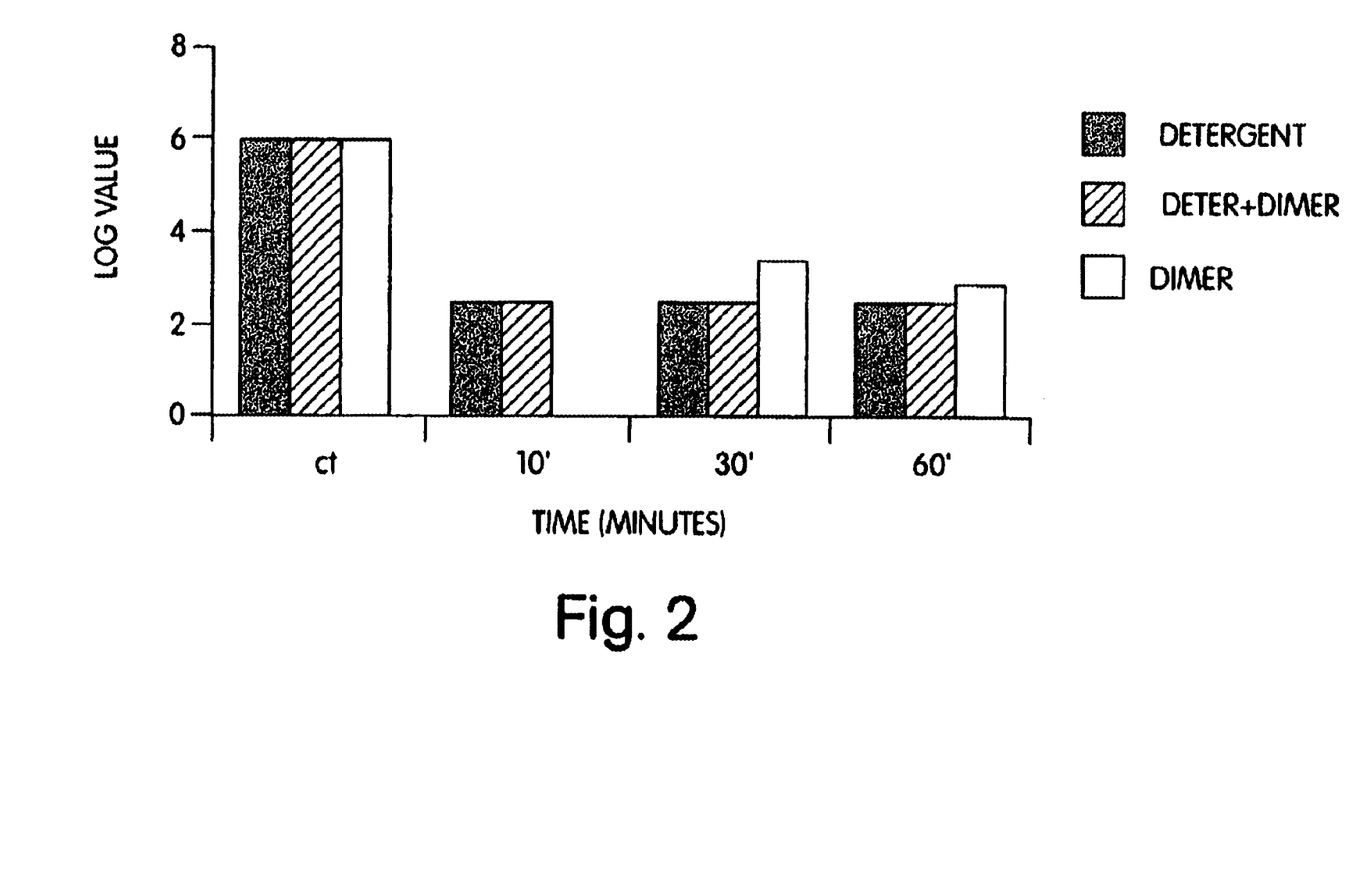
FIG. 2 is a bar graph showing log titer value versus time of treatment for BVD treated with ethyleneimine dimer, a solvent-detergent mixture, and a combination of ethyleneimine dimer and a solvent detergent mixture.

The titer of the virus was calculated as a $TCID_{50}$ (50% Tissue Culture Infections Dose) by the method of Spearman-Karber. The results are summarized in FIG. 2 (in each grouping of bars, the first bar shows detergent results; the second bar shows detergent+dimer results; and the third bar, where it appears, shows dimer results). As shown in FIG. 2, the titer dropped from 6.0 logs to 2.5 logs in the mixtures containing detergent and detergent+dimer within 10 minutes. These results show that the presence of ethyleneimine dimer does not interfere with the ability of the solvent-detergent mixture to inactivate BVD.

EXAMPLE 4
Inactivation of Porcine Parvovirus (PPV)

PPV is a non-enveloped virus; it is known to be inactivated with ethyleneimine dimer. The ability of ethyleneimine dimer to inactivate PPV in the presence of a solvent-detergent mixture was determined as follows.

A detergent stock solution (1% Tween 80, 0.3% TNBP in 0.1 M MOPS, 50 mM NaCl, pH 7.0) was prepared. A 5% dimer stock solution was prepared with 250 $\mu$l of 0.1 M MOPS, NaCl 50 mM, pH 7.0, and 12.5 $\mu$l dimer (ethyleneimine dimer, Dalton Chemical Laboratories, Inc., lot number LB-4-69A-03319). In addition, a quenching solution with a sodium thiosulphate concentration of 0.1M in 0.1 M MOPS, pH 7.0, was prepared.

(a) 9 ml 0.1 M MOPS, 50 mM NaCl, pH 7.0 was combined with 200 $\mu$l dimer stock solution. 1.0 ml PPV (PPV stock #1 filtered through 0.22$\mu$ filter) was added. The concentration of dimer in the resulting solution was 0.1%. The mixture was incubated at room temperature for a given period of time (0–3 hours). After the given time period, 1.85 ml of the solution was removed, and 0.15 ml quenching solution was added. Quenching occurred over a period of 30 minutes at room temperature. The concentration of sodium thiosulphate in the final solution was 75 mM.

(b) 9 ml detergent stock solution was combined with 1.0 ml PPV. The mixture was incubated for 0–3 hours at room temperature. A 2 ml aliquot was removed at each time point for assay.

(b') 9 ml detergent stock solution was combined with 1.0 ml PPV. The mixture was incubated for a given period of time (0–3 hours) at room temperature. After the given time period, 1.85 ml of the mixture was removed, and 0.15 ml quenching solution was added; quenching occurred over a time period of 30 minutes at room temperature. The concentration of sodium thiosulphate in the final solution was 75 mM.

(c) 9 ml detergent stock solution was combined with 200 $\mu$l dimer stock solution. 1.0 ml PPV was added. The concentration of dimer in the resulting solution was 0.1%. The mixture was incubated for a given time period (0–3 hours) at room temperature. After this period, 1.85 ml of the solution was removed and 0.15 ml quenching solution was added; quenching occurred over a period of 30 minutes at room temperature. The concentration of sodium thiosulphate in the final solution was 75 mM.

Serial 10-fold dilutions of the sample were prepared for assay. The growth medium was removed from PT-1 cells grown on 96-well plates and replaced with 100 $\mu$l of the dilutions. After 1 hour at 37° C., these dilutions were discarded and replaced with 200 $\mu$l of MEM containing 10% fetal bovine serum. The wells were cultured at 37° C. for five days, then were formalin-fixed and stained with crystal violet.

Figure 3:
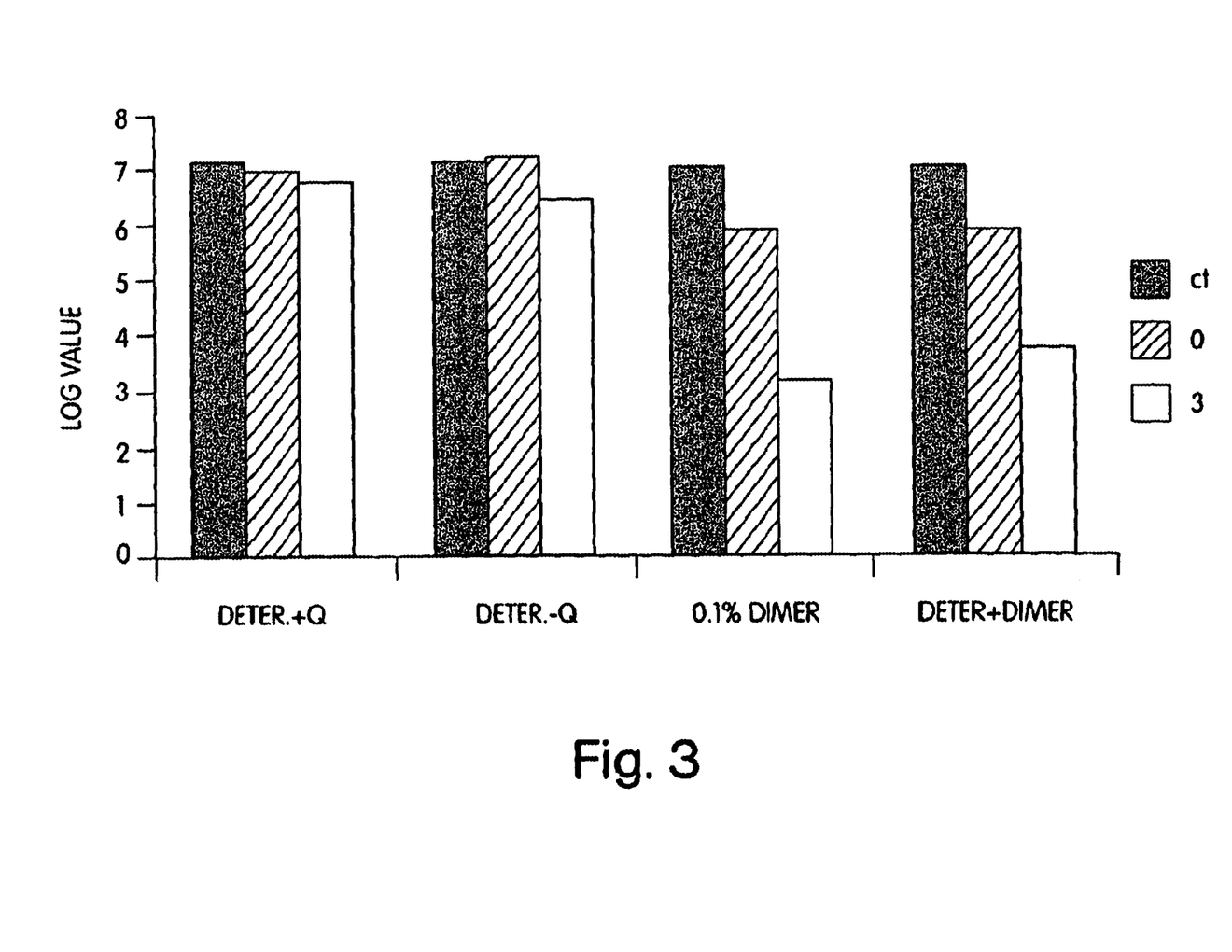
FIG. 3 is a bar graph showing log titer value versus time of treatment for PPV treated with ethyleneimine dimer, a solvent-detergent mixture, and a combination of ethyleneimine dimer and a solvent detergent mixture.

The titer of the virus was calculated as described above; the results are summarized in FIG. 3 (in each grouping of 3 bars, the first bar shows control results; the second bar shows results at 0 hours, and the third bar shows results at 3 hours). As shown there, the addition of the quenching solution had little effect on the inactivating ability of the solvent-detergent mixture. In addition, the titer dropped from 7.1 to 3.2 logs and from 7.1 to 3.8 logs, respectively, in the mixture containing dimer and the mixture containing detergent+dimer. These results show that the presence of the solvent-detergent mixture does not interfere with the ability of ethyleneimine dimer to inactivate a non-enveloped virus.

Examples 1, 3, and 4 therefore demonstrate that solvent-detergent mixtures and INACTINE™ agents are compatible compositions for inactivating phage, enveloped viruses, and non-enveloped viruses.

Other embodiments are within the claims.

What is claimed is:

1. A composition comprising an organic solvent, a non-ionic detergent, and an inactivating agent, wherein said organic solvent is selected from the group consisting of (i) trialkylphosphates of the formula $PO(OR^1)(OR^2)(OR^3)$, wherein each of $R^1$, $R^2$, and $R^3$ is, independently, $C_{1-10}$ alkyl, (ii) ethers of the formula $R^4$—O—$R^5$, wherein each of $R^4$ and $R^5$ is, independently, a $C_1$ to $C_{18}$ alkyl or alkenyl radical which can contain an oxygen or sulfur atom, and (iii) alcohols of the formula $R^6$—OH, wherein $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive, and said inactivating agent has the formula:

wherein $X_1$ is Cl or Br; $R_1$ is a divalent hydrocarbon moiety containing between 2 and 4 carbon atoms, inclusive; each of $R_2$, $R_3$, and $R_4$ is, independently, H or a monovalent hydrocarbon moiety containing between 1 and 4 carbon atoms, inclusive; $X_2$ is a pharmaceutically acceptable counter-ion; and n is an integer between 2 and 10, inclusive.

2. A composition comprising an organic solvent, a non-ionic detergent, and an inactivating agent, wherein said organic solvent is selected from the group consisting of (i) trialkylphosphates of the formula $PO(OR^1)(OR^2)(OR^3)$, wherein each of $R^1$, $R^2$, and $R^3$ is, independently, $C_{1-10}$ alkyl, (ii) ethers of the formula $R^4$—O—$R^5$, wherein each of $R^4$ and $R^5$ is, independently, a $C_1$ to $C_{18}$ alkyl or alkenyl radical which can contain an oxygen or sulfur atom, and (iii) alcohols of the formula $R^6$—OH, wherein $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive, and said inactivating agent has the formula:

wherein $X_1$ is Cl or Br; each of $R_1$, $R_3$, $R_4$, and $R_5$ is, independently, H or a monovalent hydrocarbon moiety containing between 1 and 4 carbon atoms, inclusive; $R_2$ is a divalent hydrocarbon moiety containing 3 or 4 carbon atoms; $X_2$ is a pharmaceutically acceptable counter-ion; and n is an integer between 1 and 10, inclusive.

3. A composition comprising an organic solvent, a non-ionic detergent, and an inactivating agent, wherein said organic solvent is selected from the group consisting of (i) trialkylphosphates of the formula $PO(OR^1)(OR^2)(OR^3)$, wherein each of $R^1$, $R^2$, and $R^3$ is, independently, $C_{1-10}$ alkyl, (ii) ethers of the formula $R^4$—O—$R^5$, wherein each of $R^4$ and $R^5$ is, independently, a $C_1$ to $C_{18}$ alkyl or alkenyl radical which can contain an oxygen or sulfur atom, and (iii) alcohols of the formula $R^6$—OH, wherein $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive, and said inactivating agent has the formula:

wherein each of $R_1$, $R_2$, $R_3$, $R_4$, $R_6$, $R_7$, and $R_8$ is, independently, H or alkyl, provided that $R_1$, $R_2$, $R_3$, $R_4$, $R_6$, $R_7$, and $R_8$ cannot all be H; $R_5$ is alkylene: X is a pharmaceutically acceptable counter-ion; and n is an integer between 1 and 10, inclusive.

4. A composition comprising an organic solvent, a non-ionic detergent, and an inactivating agent, wherein said organic solvent is selected from the group consisting of (i) trialkylphosphates of the formula $PO(OR^1)(OR^2)(OR^3)$, wherein each of $R^1$, $R^2$, and $R^3$ is, independently $C_{1-10}$ alkyl, (ii) ethers of the formula $R^4$—O—$R^5$, wherein each of $R^4$ and $R^5$ is, independently, a $C_1$ to $C_{18}$ alkyl or alkenyl radical which can contain an oxygen or sulfur atom, and (iii) alcohols of the formula $R^6$—OH, wherein $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive, and said inactivating agent has the formula:

wherein each of $R_1$, $R_2$, $R_3$, $R_4$, $R_6$, $R_7$, and $R_8$ is, independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms, inclusive; X is a pharmaceutically acceptable counter-ion; and n is 2 or 3.

5. A composition comprising an organic solvent, a non-ionic detergent, and an inactivating agent, wherein said organic solvent is selected from the group consisting of (i) trialkylphosphates of the formula $PO(OR^1)(OR^2)(OR^3)$, wherein each of $R^1$, $R^2$, and $R^3$ is,independently, $C_{1-10}$ alkyl, (ii) ethers of the formula $R^4$—O—$R^5$, wherein each of $R^4$ and $R^5$ is, independently, a $C_1$ to $C_{18}$ alkyl or alkenyl radical which can contain an oxygen or sulfur atom, and (iii) alcohols of the formula $R^6$—OH, wherein $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive, and said inactivating agent has the formula:

wherein each of $R_1$, $R_2$, $R_3$, $R_4$, $R_6$, $R_7$, and $R_8$ independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms, inclusive; X is a pharmaceutically acceptable counter-ion; and n is an integer between 1 and 10, inclusive, wherein said organic solvent is a trialkylphosphate of the formula $PO(OR^1)(OR^2)(OR^3)$, wherein each of $R^1$, $R^2$, and $R^3$ is, independently, $C_{1-10}$ alkyl.

6. A composition comprising an organic solvent, a non-ionic detergent, and an inactivating agent, wherein said organic solvent is selected from the group consisting of (i) trialkylphosphates of the formula $PO(OR^1)(OR^2)(OR^3)$, wherein each of $R^1$, $R^2$, and $R^3$ is, independently, $C_{1-10}$ alkyl, (ii) ethers of the formula $R^4$—O—$R^5$, wherein each of $R^4$ and $R^5$ is, independently, a $C_1$ to $C_{18}$ alkyl or alkenyl radical which can contain an oxygen or sulfur atom, and (iii) alcohols of the formula $R^6$—OH, wherein $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive, and said inactivating agent has the formula:

wherein each of $R_1$, $R_2$, $R_3$, $R_4$, $R_6$, $R_7$, and $R_8$ is, independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms, inclusive, X is a pharmaceutically acceptable counter-ion; and n is an integer between 1 and 10, inclusive, wherein said organic solvent is tri-n-butyl phosphate.

7. A composition comprising an organic solvent, a non-ionic detergent, and an inactivating agent, wherein said organic solvent is selected from the group consisting of (i) trialkylphosphates of the formula $PO(OR^1)(OR^2)(OR^3)$, wherein each of $R^1$, $R^2$, and $R^3$ is, independently, $C_{1-10}$ alkyl, (ii) ethers of the formula $R^4$—O—$R^5$, wherein each of $R^4$ and $R^5$ is, independently, a $C_1$ to $C_{18}$ alkyl or alkenyl radical which can contain an oxygen or sulfur atom, and (iii) alcohols of the formula $R^6$—OH, wherein $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive, and said inactivating agent has the formula:

wherein each of $R_1$, $R_2$, $R_3$, $R_4$, $R_6$, $R_7$, and $R_8$ is, independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms, inclusive; X is a pharmaceutically acceptable counter-ion; and n is an integer between 1 and 10, inclusive, wherein said organic solvent is an ether of the formula $R^4$—O—$R^5$, wherein each of $R^4$ and $R^5$ is, independently, a $C_1$ to $C_{18}$ alkyl or alkenyl radical which can contain an oxygen or sulfur atom.

8. The composition of claim 9, wherein each of $R^4$ and $R^5$ is, independently, a $C_1$ to $C_8$ alkyl radical.

9. A composition comprising an organic solvent, a non-ionic detergent, and an inactivating agent, wherein said organic solvent is selected from the group consisting of (i) trialkylphosphates of the formula PO($OR^1$)($OR^2$)($OR^3$), wherein each of $R^1$, $R^2$, and $R^3$ is, independently, $C_{1-10}$ alkyl, (ii) ethers of the formula $R^4$—O—$R^5$, wherein each of $R^4$ and $R^5$ is, independently, a $C_1$ to $C_{18}$ alkyl or alkenyl radical which can contain an oxygen or sulfur atom, and (iii) alcohols of the formula $R^6$—OH, wherein $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive, and said inactivating agent has the formula:

wherein each of $R_1$, $R_2$, $R_3$, $R_4$, $R_6$, $R_7$, and $R_8$ is independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms, inclusive; X is a pharmaceutically acceptable counter-ion; and n is an integer between 1 and 10, inclusive, wherein said organic solvent is an alcohol of the formula $R^6$—OH, wherein $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive.

10. The composition of claim 9, wherein $R^6$ is a $C_1$ to $C_8$ alkyl radical.

11. A composition comprising an organic solvent, a non-ionic detergent, and an inactivating agent, wherein said organic solvent is selected from the group consisting of (i) trialkylphosphates of the formula PO($OR^1$)($OR^2$)($OR^3$), wherein each of $R^1$, $R^2$, and $R^3$ is, independently, $C_{1-10}$ alkyl, (ii) ethers of the formula $R^4$—O—$R^5$, wherein each of $R^4$ and $R^5$ is, independently, a $C_1$ to $C_{18}$ alkyl or alkenyl radical which can contain an oxygen or sulfur atom, and (iii) alcohols of the formula $R^6$—OH, wherein $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive, and said inactivating agent has the formula:

wherein each of $R_1$, $R_2$, $R_3$, $R_4$, $R_6$, $R_7$, and $R_8$ is, independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms, inclusive; X is a pharmaceutically acceptable counter-ion; and n is an integer between 1 and 10, inclusive, wherein the non-ionic detergent is polyoxyethylene sorbitan monooleate.

12. A composition comprising an organic solvent, a non-ionic detergent, and an inactivating agent, wherein said organic solvent is selected from the group consisting of (i) trialkylphosphates of the formula PO($OR^1$)($OR^2$)($OR^3$), wherein each of $R^1$, $R^2$, and $R^3$ is, independently, $C_{1-10}$ alkyl, (ii) ethers of the formula $R^4$—O—$R^5$, wherein each of $R^4$ and $R^5$ is, independently, a $C_1$ to $C_{18}$ alkyl or alkenyl radical which can contain an oxygen or sulfur atom, and (iii) alcohols of the formula $R^6$—OH, wherein $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive, and said inactivating agent has the formula:

wherein each of $R_1$, $R_2$, $R_3$, $R_4$, $R_6$, $R_7$, and $R_8$ is, independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms; inclusive; X is a pharmaceutically acceptable counter-ion; and n is an integer between 1 and 10, inclusive, wherein said organic solvent is present in a concentration of about 0.1% to about 0.5% (v/v), and said inactivating agent is present in a concentration of about 0.0005 M to about 0.005 M.

13. The composition of claim 1, wherein $R_1$ is alkylene and each of $R_2$, $R_3$, and $R_4$ is, independently, H or alkyl.

14. The composition of claim 1, wherein $R_1$ is ethylene; $R_2$, $R_3$, and $R_4$ are H; and n is 3 or 4.

15. The composition of claim 1, wherein said organic solvent is a trialkylphosphate of the formula PO($OR^1$)($OR^2$)($OR^3$), wherein each of $R^1$, $R^2$, and $R^3$ is, independently, $C_{1-10}$ alkyl.

16. The composition of claim 1, wherein said organic solvent is tri-n-butyl phosphate.

17. The composition of claim 1, wherein said organic solvent is an ether of the formula $R^4$—O—$R^5$, wherein each of $R^4$ and $R^5$ is, independently, a $C_1$ to $C_{18}$ alkyl or alkenyl radical which can contain an oxygen or sulfur atom.

18. The composition of claim 17, wherein each of $R^4$ and $R^5$ is, independently, a $C_1$ to $C_8$ alkyl radical.

19. The composition of claim 1, wherein said organic solvent is an alcohol of the formula $R^6$—OH, wherein $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive.

20. The composition of claim 19, wherein $R^6$ is a $C_1$ to $C_8$ alkyl radical.

21. The composition of claim 1, wherein the non-ionic detergent is polyoxyethylene sorbitan monooleate.

22. The composition of claim 1, wherein said organic solvent is present in a concentration of about 0.1% to about 0.5% (v/v), and said inactivating agent is present in a concentration of about 0.0005 M to about 0.005 M.

23. The composition of claim 2, wherein each of $R_1$, $R_3$, $R_4$, and $R_5$ is, independently, H or alkyl, and $R_2$ is alkylene.

24. The method of claim 23, wherein $R_2$ contains 3 carbon atoms.

25. The method of claim 23, wherein n is 2 or 3.

26. The composition of claim 2, wherein said organic solvent is a trialkylphosphate of the formula $PO(OR^1)(OR^2)(OR^3)$, wherein each of $R^1$, $R^2$, and $R^3$ is, independently, $C_{1-10}$ alkyl.

27. The composition of claim 2, wherein said organic solvent is tri-n-butyl phosphate.

28. The composition of claim 2, wherein said organic solvent is an ether of the formula $R^4$—O—$R^5$, wherein each of $R^4$ and $R^5$ is, independently, a $C_1$ to $C_{18}$ alkyl or alkenyl radical which can contain an oxygen or sulfur atom.

29. The composition of claim 28, wherein each of $R^4$ and $R^5$ is, independently, a $C_1$ to $C_8$ alkyl radical.

30. The composition of claim 2, wherein said organic solvent is an alcohol of the formula $R^6$—OH, wherein $R^6$ is a $C_1$ to $C_{18}$ alkyl or alkenyl radical which can contain 1 to 4 oxygen or sulfur atoms, inclusive, in the chain, and which can be substituted by 1 to 4 hydroxy groups, inclusive.

31. The composition of claim 30, wherein $R^6$ is a $C_1$ to $C_8$ alkyl radical.

32. The composition of claim 2, wherein the non-ionic detergent is polyoxyethylene sorbitan monooleate.

33. The composition of claim 2, wherein said organic solvent is present in a concentration of about 0.1% to about 0.5% (v/v), and said inactivating agent is present in a concentration of about 0.0005 M to about 0.005 M.

* * * * *